(12) United States Patent
Seguin

(10) Patent No.: US 9,427,236 B2
(45) Date of Patent: Aug. 30, 2016

(54) METHODS AND APPARATUS USING AN ANCHORED BALLOON FOR TREATING PULMONARY ARTERIAL HYPERTENSION

(71) Applicant: Jacques Seguin, Launen bei Gstaad (CH)

(72) Inventor: Jacques Seguin, Launen bei Gstaad (CH)

( * ) Notice: Subject to any disclaimer, the term of this patent is extended or adjusted under 35 U.S.C. 154(b) by 0 days.

(21) Appl. No.: 14/594,021

(22) Filed: Jan. 9, 2015

(65) Prior Publication Data
US 2015/0216531 A1    Aug. 6, 2015

Related U.S. Application Data

(63) Continuation of application No. PCT/IB2015/050068, filed on Jan. 5, 2015.

(30) Foreign Application Priority Data

Jan. 31, 2014  (FR) ...................... 14 50786

(51) Int. Cl.
*A61B 17/12*     (2006.01)
*A61M 25/10*     (2013.01)

(52) U.S. Cl.
CPC ... *A61B 17/12136* (2013.01); *A61B 17/12036* (2013.01); *A61B 17/12109* (2013.01); *A61B 2017/1205* (2013.01)

(58) Field of Classification Search
CPC .................. A61B 17/12022; A61B 17/12031; A61B 17/12036; A61B 17/1204; A61B 17/12099; A61B 17/12109; A61B 17/12122; A61B 17/12131; A61B 17/12136; A61B 2017/1205; A61M 25/10; A61M 25/1002; A61M 25/1011; A61M 25/10182; A61M 25/1025; A61M 25/104; A61M 2025/1015; A61M 2025/1045
See application file for complete search history.

(56) References Cited

U.S. PATENT DOCUMENTS 4,902,273 A    2/1990 Choy et al.
5,112,303 A    5/1992 Pudenz et al.
(Continued)

FOREIGN PATENT DOCUMENTS

CN    102657910 A    9/2012
DE    19508129 A1    9/1996
(Continued)

OTHER PUBLICATIONS

International search report and written opinion dated Mar. 24, 2015 for PCT/IB2015/050066.
International search report and written opinion dated Mar. 24, 2015 for PCT/IB2015/050068.
(Continued)

*Primary Examiner* — Ryan J Severson
(74) *Attorney, Agent, or Firm* — Wilson Sonsini Goodrich & Rosati

(57) ABSTRACT

A device (1) includes at least an inflatable balloon (2), an implantable port (2A), and a conduit (3) intended for connecting the balloon (2) and the implantable port in a sealed manner. The balloon (2), the port (2A), and the conduit (3) are filled with a gas, and the pressure is such that the balloon (1) is normally inflated but is capable of being compressed during systole. A catheter (5) slidingly carries the balloon (2) in a deflated condition. At least one anchoring member (6) is connected to an actuating wire (7) which is slidable in the catheter independently of the balloon (2). The conduit (3) and said actuating wire (7) are connected to the catheter (5) to either prevent or allow sliding of this conduit and of this actuating wire relative to the catheter (5).

7 Claims, 4 Drawing Sheets

(56) References Cited

U.S. PATENT DOCUMENTS

| | | |
|---|---|---|
| 5,833,655 A | 11/1998 | Freed et al. |
| 6,017,324 A | 1/2000 | Tu et al. |
| 6,053,891 A | 4/2000 | Decampli |
| 6,558,349 B1 † | 5/2003 | Kirkman |
| 6,576,007 B2 | 6/2003 | Dehdashtian et al. |
| 6,579,224 B1 | 6/2003 | Burton et al. |
| 7,468,050 B1 | 12/2008 | Kantrowitz |
| 8,876,850 B1 | 11/2014 | Vollmers et al. |
| 2004/0093007 A1* | 5/2004 | Sussman .......... A61B 17/12045 606/194 |
| 2006/0129083 A1 | 6/2006 | Brenneman et al. |
| 2006/0241745 A1 † | 10/2006 | Solem |
| 2013/0245665 A1 † | 9/2013 | Scandurra |
| 2015/0196303 A1 | 7/2015 | Seguin |

FOREIGN PATENT DOCUMENTS

| | | |
|---|---|---|
| DE | 102005060197 A1 | 6/2007 |
| EP | 0366814 A1 | 5/1990 |
| WO | WO 90/06086 A1 | 6/1990 |
| WO | WO 96/12518 A1 | 5/1996 |
| WO | WO 93/17731 A1 | 9/1996 |
| WO | WO 96/34647 A1 | 11/1996 |
| WO | WO 98/50100 A1 | 11/1998 |
| WO | WO 00/66030 A1 | 11/2000 |
| WO | WO 2012/071395 A1 * | 5/2012 |
| WO | WO 2013/185138 A1 | 12/2013 |

OTHER PUBLICATIONS

Office action dated Sep. 28, 2015 for U.S. Appl. No. 14/594,012.

* cited by examiner
† cited by third party

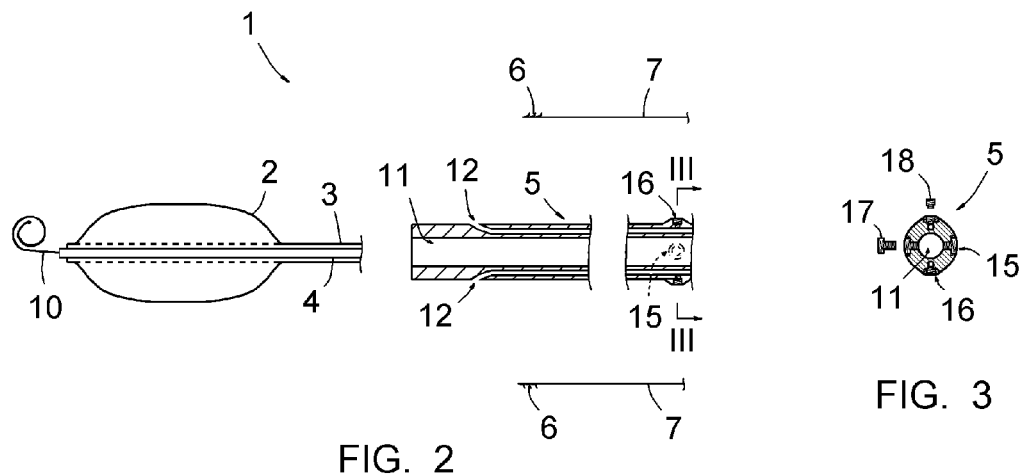
FIG. 2
FIG. 3
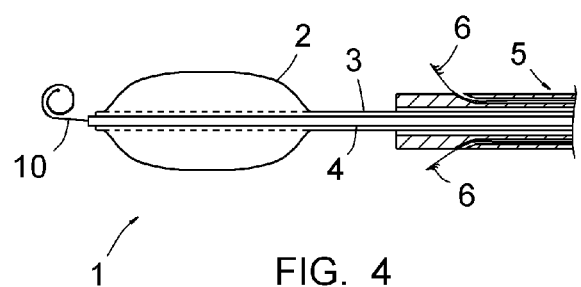
FIG. 4
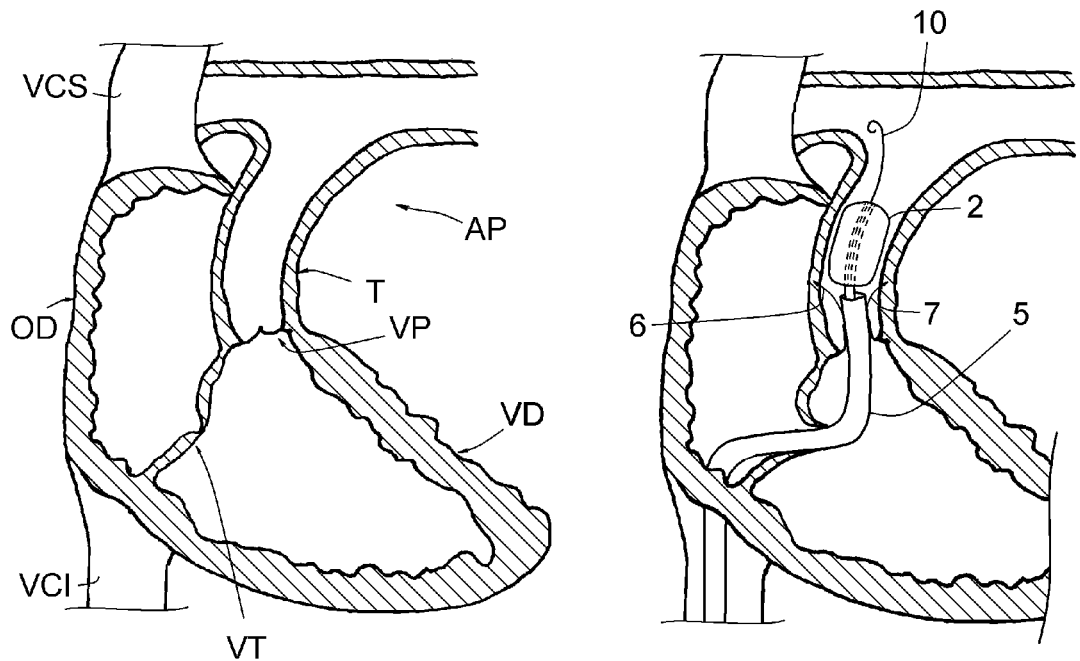
FIG. 5
FIG. 6

METHODS AND APPARATUS USING AN ANCHORED BALLOON FOR TREATING PULMONARY ARTERIAL HYPERTENSION

CROSS-REFERENCE TO RELATED APPLICATIONS

This application is a continuation of International Patent Application No. PCT/IB2015/050068, filed Jan. 5, 2015, which claims priority to FR Patent Application No. 1450786 (1000226086), filed Jan. 31, 2014, the contents of which are incorporated herein by reference.

BACKGROUND OF THE INVENTION

1. Field of the Invention

The present invention relates generally to medical devices and methods. More particularly, the present invention relates to a device for the treatment of pulmonary arterial hypertension.

Pulmonary arterial hypertension is a disease that affects a large number of people, either directly through pulmonary fibrosis or indirectly as a result of respiratory failure or left ventricular failure. Pulmonary arterial hypertension usually results from an increase in peripheral pulmonary vascular resistance and a decrease in pulmonary arterial compliance.

One approach for treating pulmonary hypertension relies on placing a balloon in the trunk of the pulmonary artery, or two balloons in the branches of the pulmonary artery bifurcation. The balloon(s) are connected to an implantable port and are normally inflated with a gas to partially extend across the trunk or the branches. The port will hold excess gas that provides a "gas reserve." The balloon(s) are fully expanded during right ventricular diastole, and thus will limit the backflow of blood. During right ventricular systole, however, the balloons compress in response to the increased blood pressure so that they do no significantly impede the flow of blood into the pulmonary artery. Such compression temporarily generates an overpressure which is mitigated by the excess volume provided by the implantable port as well as by the conduit connecting the port to the balloon.

While quite effective for treating pulmonary hypertension, the placement of these balloons in the trunk or the branches of the pulmonary artery can be difficult. In particular, with present balloon designs and placement protocols, the balloons may become displaced during systole or diastole, and such displacement can reduce device efficiency and in some cases cause vascular trauma. Moreover, the present devices can be difficult to remove and replace if they become leak or otherwise become dysfunctional over time.

For these reasons, it would be desirable to provide improved pulmonary artery balloon catheter designs and placement protocols which minimize the risks associated with balloon mobility. The balloon designs should also be amenable to replacement should that become necessary. The present invention will meet at least some of these objectives.

2. Description of the Background Art

Pulmonary arterial catheters and other devices are described in U.S. Pat. Nos. 4,902,273; 6,017,324; 6,053,891; and 8,876,850; and PCT Applications WO 1993/17731 and 2013/185138.

SUMMARY OF THE INVENTION

In a first aspect of the present invention, a system for treating pulmonary hypertension comprises an implantable port configured for subcutaneous implantation and having an internal chamber. A guide conduit is attached at one end to the implantable port and an inflatable balloon is attached at another end of the guide conduit to receive an inflation medium therefrom. A catheter slidably receives the guide conduit and inflatable balloon, and an element for anchoring at least one of the catheter and the inflatable balloon when the balloon is partially inflated within the pulmonary artery.

In certain embodiment, the system further comprises a second guide conduit and a second inflatable balloon which are slidably received in the catheter. The anchoring element or other means may comprise at least one tissue-penetrating barb that is configured to be laterally deployed from a distal end of the catheter to anchor within a trunk region of the pulmonary artery, further optionally including a pair of tissue-penetrating barbs that laterally deploy from opposite sides of the distal end of the catheter.

The anchoring element or other means may alternatively comprises a self-expanding anchor that is configured to be advanced from a distal tip of the inflatable balloon, wherein the self-expanding anchor is radially constrained within the balloon and self-expands to open radially and anchor within the pulmonary artery. Typically, the self-expanding anchor has a stent-like structure which expands to circumferentially engage an annular wall segment of the pulmonary artery.

In still further embodiments, the anchoring element or other means may comprise at least one tissue-penetrating element that is configured to be deployed from the catheter to anchor within the heart. The at least one tissue-penetrating element may, for example, comprise a helical structure that is configured to be screwed into a heart wall. In these further embodiments, the catheter may have a T-branch that is configured to lie within the heart chamber, wherein one branch of the T extends into the pulmonary artery to deploy the inflatable balloon and the other branch of the T is open to deploy the at least one tissue-penetrating element.

The use of these anchors will inhibit displacement of the balloon after deployment, and the specific anchor designs are relatively easy to remove to facilitate replacement, particularly the stent-like anchor.

In a second aspect of the present invention, a method as for treating pulmonary hypertension comprises advancing a catheter through a heart chamber into a pulmonary artery, advancing an inflatable balloon through the catheter and into the pulmonary artery, anchoring the catheter and/or the inflatable balloon within at least one of the heart chamber and the pulmonary artery, and filling the inflatable balloon with a gas or other compressible filling medium so that the balloon will partially occupy either a trunk or a branch of the pulmonary artery and will partially collapse during systole. Optionally, another inflatable balloon may be advanced balloon through the catheter and into the pulmonary artery, where one inflatable balloon occupies a left branch of the pulmonary artery and the other inflatable balloon occupies a right branch of the pulmonary artery. The placement of the anchor inhibits displacement of the balloon(s) after deployment, and the specific anchor designs are relatively easy to remove to facilitate replacement, particularly the stent-like anchor.

In specific embodiments, anchoring may comprise advancing at least one barb from the catheter to penetrate into a wall region of the pulmonary artery. The target wall region may be in a trunk of the pulmonary artery, and often at least two barbs are advanced from the catheter to penetrate into the target wall region/

In alternative specific embodiments, anchoring may comprise advancing a self-expanding anchor from a distal tip of the inflatable balloon so that the anchor expands and anchors against a wall region of the pulmonary artery. The self-expanding anchor may comprise a tubular scaffold that is radially compressed within the inflatable balloon and which self-expands when released from constraint. Optionally, the self-expanding anchor may self-expands with a trunk or a branch of the pulmonary artery.

In still further alternative embodiments, at least one tissue-penetrating element may be advanced from the catheter into a wall of the heart chamber. For example, the tissue-penetrating element may be helical and may be screwed into the heart chamber wall. The at least one tissue-penetrating element may be advanced from one branch of a T-branch in the catheter and the inflatable balloon may be advanced through another branch of the T-branch.

In more detailed implementations of the present invention, the system further comprises:
at least one anchoring member for anchoring to the pulmonary artery or to the wall of the heart, connected to an actuating wire that is slidable in the catheter, this anchoring member being movable, independently from the balloon, between a retracted position in the catheter, in which the anchoring member is retracted in the catheter and does not perform any anchoring, and an anchoring position in which the anchoring member is extended from the catheter and performs an anchoring function, and
connecting means for connecting the said conduit and the said actuating wire to the catheter, making it possible, in an active position, to block the sliding of this conduit and of this actuating wire relative to the catheter, and, in an inactive position, to release this sliding.

The invention thus consists of designing a device wherein the balloon is capable of sliding in a catheter independently from the anchoring member or members providing the ability to fix this balloon relative to the heart, this or these anchoring members being also capable of sliding in the catheter, and to provide the connecting means for selectively connecting the said conduit and the said actuating wire to the catheter. When these connecting means are in the active position, the balloon is locked and immovable relative to the catheter, which is itself immobilized in relation to the anchoring member, with the result thereof being that the balloon is anchored relative to the heart and is not at risk of migrating under the effect of the repeated stresses to which it is subjected. When the said connecting means are in the inactive position, the balloon is thus movable relative to the catheter and is therefore capable of being repositioned appropriately, if necessary, or may even be deflated and extracted through the catheter so as to be interchanged.

The connection means may be such that, in the active position, they simultaneously block the sliding of the said conduit and of the said actuating wire in the catheter: preferably, however, these connecting means comprise a first set of connecting means making it possible to block the sliding of the said conduit in the catheter, and a second set of connecting means, that are capable to be actuated independently from the first set of connecting means, making it possible to block the sliding of the said actuating wire.

These two separate sets of connecting means thus make it possible to maintain the connection of the catheter to the anchoring member, and therefore the immobilization of the catheter relative to the heart, when a sliding motion the balloon relative to the balloon catheter is brought about.

According to a first embodiment of the invention, the system comprises:
a plurality of anchoring members, each of which being in the form of a portion of wire that is harpoon-shaped, connected to the actuating wire in the continuity thereof, and
deflection means for the lateral deflection of these anchoring members and of the portions of the actuating wires connected thereto with respect to the catheter, in a manner such that the anchoring members, during the sliding thereof towards the said anchoring position, are directed laterally in relation to the catheter.

In practice, the device according to this first embodiment is introduced into the heart up to such point as the catheter has passed through the pulmonary valve, and then the anchoring members are deployed to their anchoring position, in which they are inserted in the wall of the pulmonary artery.

According to one possibility, the deflection means can be comprised of a curvature of the end portion of the actuating wires and of a resilient structure of these actuating wires. The actuating wires are thus elastically deformed when they are engaged in the catheter and return to their normal curved shape when they are slid towards the said anchoring position.

Alternatively, each anchoring member, and the actuating wire connected thereto, is slidable in a tubular sheath arranged in the wall of the catheter, and each tubular sheath comprises a curved outlet portion, orientated radially outward from the catheter, forming the said deflection means.

Each curved outlet portion allows for the deflection of the portion of the actuating wire connected to the anchoring member when this anchoring member and this wire are moved to the said anchoring position.

According to another embodiment of the invention:
the balloon comprises a guide tube extending therethrough, from one end to the opposite end thereof;
each anchoring member is in the form of an extendable tubular portion connected to an actuating wire, the said tubular portion being deformable between a contracted position, wherein it is adapted to be engaged and to slide in the said guide tube, and a deployed position, in which this tubular portion has a diameter greater than the diameter of a body conduit into which it is to be implanted.

The body conduit is either the trunk of the pulmonary artery or one of the branches formed by this artery downstream of the bifurcation thereof.

In practice, the device according to this other embodiment is introduced in the heart up to such point as the catheter has passed through the pulmonary valve, the balloon is then deployed from the catheter, and the anchoring member associated with this balloon is slid in the guide tube of the balloon, up to a position beyond the balloon. This member is then deployed against the wall of the pulmonary artery, so as to immobilize the entire device, and therefore the balloon, in relation to this artery.

The said expandable tubular portion may notably be self-expanding, by means of the elastic restoring force or shape memory, in the manner well known in the field of stents.

According to yet another embodiment of the invention, the catheter forms, at its end intended to be inserted into a heart, two openings arranged to open laterally, on two radially opposite sides of the catheter, a first of the said openings being adapted to let through the said balloon and the second opening being adapted to let through the anchoring member and the actuating wire connected to this anchoring member.

In this case, the catheter has thus a "T"-shaped end or a "bifurcated" end, and is intended to be simply engaged in the right ventricle of a heart, the first opening thereof is intended to be directed towards the pulmonary valve, for the deployment of one or two balloon(s) in the pulmonary artery, through this valve; second opening is then directed towards the wall of the ventricle and is used to direct the anchoring member in the direction of this wall.

In this case, this anchoring member may be constituted by a-spring-shaped anchor capable of being inserted in the wall of the ventricle of a heart.

On an optional basis,
the said balloon is dimensioned so as to be set in place in one of the branches of the pulmonary artery, and
the device comprises a second balloon, dimensioned so as to be set in place in the other of the branches of the pulmonary artery, and a second conduit intended for connecting this second balloon to the said implantable port in a sealed manner, the said catheter being adapted to receive therein, with sliding capability, the two balloons in deflated state as well as these two conduits, and the said connection means being adapted, in the said active position, to block the sliding of these two conduits, and, in the said inactive position, to release the sliding of these two conduits.

The device thus configured comprises two balloons to be placed in the two respective branches of the pulmonary artery.

The invention will be better understood, and other characteristic features and advantages thereof will appear, with reference made to the accompanying drawing which shows, by way of non-limiting examples, several possible embodiments of the device concerned.

BRIEF DESCRIPTION OF THE DRAWINGS

FIG. 2 show different views of various different elements forming this device according to a second embodiment, these elements being separated from each other;

FIG. 3 is a sectional view taken along the line III-III of FIG. 2, further showing the screws 17, 18 in a position out of their receiving holes;

FIG. 4 is a view of the said elements in their mounting state;

FIG. 5 is a section view of a right heart;

FIG. 6 is a view of the heart similar to that in FIG. 5, during a step in the process to set the device in place;

DETAILED DESCRIPTION OF THE INVENTION

Figure 1:
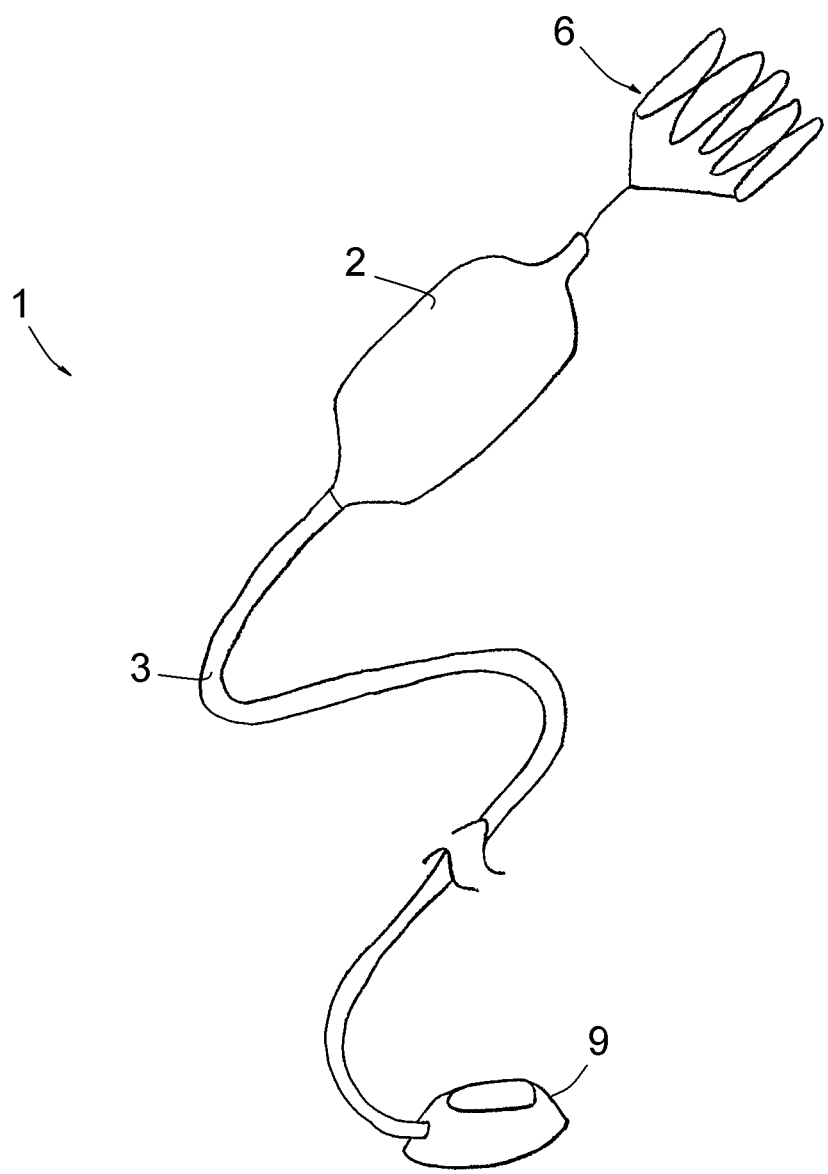
FIG. 1 is a view of this device according to a first embodiment.

FIG. 1 show a device 1 for the treatment of pulmonary arterial hypertension, comprising an inflatable balloon 2, an implantable port 9 and a conduit 3 intended for connecting the balloon and the implantable port in a sealed manner.

FIG. 1 also shows an anchoring member 6 in the form of an extendable tubular portion formed of a zigzag wire, which will be described later, with reference to FIGS. 7-9.

On FIGS. 2-4 is shown a device 1 according to an embodiment comprising a guide tube 4 and a catheter 5, and in which the anchoring member is in the form of two harpoon-shaped anchoring members 6, connected to respective actuating wires 7.

The balloon 2 is connected in a sealed manner to the conduit 3 at its longitudinal ends, in particular by welding. In the example shown, it is meant to be placed in the trunk T of the pulmonary artery AP (see FIGS. 5 and 6), and has a circular cross-section, the area of which, in the inflated state of the balloon, occupies, in a purely indicative manner, about 50% to 70% of the surface area of the cross section of the trunk T.

The implantable port 9 is of a well-known type, comprising a body and a membrane which together define an empty space forming the port itself. The membrane is intended to extend under the patient's skin and can be pricked by the needle of a syringe in order to introduce gas, in particular helium or $CO_2$, in the said empty space.

The conduit 3 extends inside the balloon 2 and is perforated at its portion located inside the balloon, so as to permit inflation of the balloon through its wall. It is designed to be engaged through the catheter 5 and is slidable in relation to the latter. It extends beyond the end of the catheter 5 not intended to be engaged in a heart, and is connected to the said implantable port.

The guide tube 4 is engaged in the conduit 3 and extends up to the end of the balloon opposite the catheter 5, at which end it opens out to the exterior of the balloon. At this end, it is connected in a sealed manner to the tube 3, in particular welded thereto, so as to close off the volume delimited by the balloon 2. It is intended to receive a guide wire 10 and makes possible the through passage and the sliding of this guide wire beyond the balloon 2.

According to a well-known technique, this guide wire 10 is preformed so as to form a loop at its free end when it is not constrained in the tube 4, in order not to cause injury or perforating of the wall of the pulmonary artery AP.

The catheter 5 internally defines a passage 11 in which can be received the balloon 2 in the deflated state and the conduit 3, and comprises two diametrically opposed peripheral tubular sheaths, within each of which are intended to be engaged and slide one of the said anchoring members 6 and the actuating wire 7 connected thereto. Each tubular sheath has a curved outlet portion 12, directed radially outwards towards the exterior of the catheter 5, making possible the deflection of the portion of the actuating wire 7 connected to the anchoring member 6 when this wire and this anchoring member are moved to an anchoring position, as can be seen in FIGS. 4 and 6.

On the side of the end thereof not intended to be introduced into a heart, as is shown more particularly in FIG. 3, the catheter 5 comprises metal washers embedded in its wall, which have tapped holes 15, 16 borne in them, meant for receiving the respective blocking screws 17, 18 (only one screw 17 and one screw 18 are shown). The holes 15 of a first pair of washers are diametrically opposed to each other and open out into the conduit 11. The holes 16 of the second pair of washers are diametrically opposed to each other and have their axes perpendicular to the axes of the holes 15; they open out into the abovementioned tubular sheaths.

The two screws 17 intended to be engaged in the holes 15, come to bear against the conduit 3 when they are tightened, and thus make it possible to block the sliding of this conduit 3 in the passage 11; when they are loosened, they do not cause any hindrance to this sliding. Similarly, when they are tightened, the two screws 18 intended to be engaged in the holes 16, come to bear against the wires 7 and thus make it possible to block the sliding of these wires in the tubular sheath; when they are loosened, they do not cause any hindrance to this sliding.

Each anchoring member 6 is formed by an end portion of the wire 7 on which are arranged sharp protuberances that cause this portion to be harpoon-shaped.

Each actuating wire 7 is metallic and has a degree of elastic flexibility such that it may be deflected as shown in FIG. 4.

The FIG. 5 shows a sectional view of a right heart. Recognizable in the figure are the superior vena cava VCS, the right atrium OD, the inferior vena cava VCI, the tricuspid valve VT, the right ventricle VD, the pulmonary valve VP, the trunk T of the pulmonary artery AP and the left branch and the right branch of this artery, formed by the bifurcation thereof.

The device 1 previously described above is implanted in place by means of the following procedure.

The catheter 5 containing the balloon 2 in the deflated and folded state is inserted in the inferior vena cava, through the tricuspid valve, into the right ventricle, across the pulmonary valve, and right through into the trunk of the pulmonary artery, and the wire 10 is then deployed. The screws 17, 18 in the respective holes 15 and 16 are then loosened.

The balloon 2 is then pushed out of the catheter 5 by means of a sliding pusher introduced into this catheter 5, until the point where it is fully released and free from the latter, which engages the balloon 2 on the guide wire 10, by sliding the tube 4 on this guide wire.

The actuating wires 7 are then pushed so as to insert the anchoring members 6 in the wall of the trunk of the pulmonary artery PA, see FIG. 6.

The guide wire 10 is removed, the screws 17 and 18 in the holes 15 and 16 are tightened and the port 9 is implanted and connected in a sealed manner to the conduit 3. Gas is then introduced in this port 9, in this conduit 3 and in the balloon 2, this introduction of gas being carried out at the pressure level that makes it possible for the balloon 2 to be inflated during the right ventricular diastole, see FIG. 6, but for it to be compressed during the right ventricular systole, under the pressure which the flow of blood exerts on it. This compression temporarily generates an overpressure in the said implantable port 9 and the said conduit 3.

The device according to the invention, so implanted, makes possible an increase in the diastolic pressure of the pulmonary artery, a decrease of the systolic pressure of the pulmonary artery, an increase of the arterial compliance and an immediate and sustained increase in the cardiac output, without the risk of mobility of the balloon 1. The latter is perfectly held in position by the anchoring of the catheter 5 achieved by means of the anchoring members 6.

If necessary, the screws 17 may be loosened so as to allow correction of the position of the balloon 2, or even a withdrawal of this balloon after deflation, through the catheter 5, may be effected with a view to an interchange.

Figure 7:
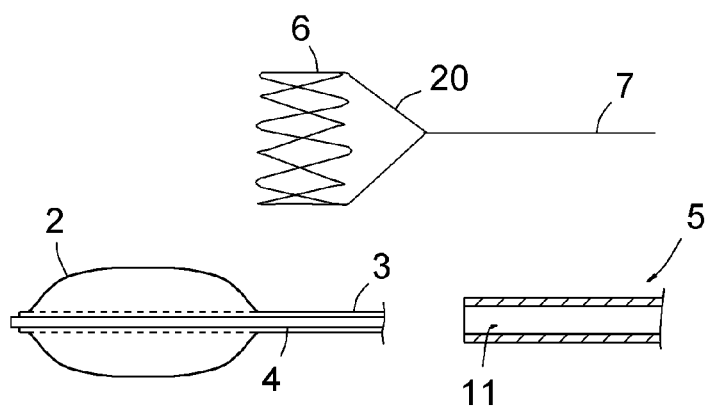
FIG. 7 is a view similar to that in FIG. 2 of a device according to said first embodiment.

FIG. 7 shows the device 1 according to the embodiment of FIG. 1, which comprises as above a balloon 2, a conduit 3, a guide tube 4, a catheter 5, the afore-mentioned anchoring member 6, and an actuating wire 7 connected to this anchoring member 6. For the purposes of simplification, the elements or parts that are identical or similar to those previously described above are designated by the same reference numerals.

The balloon 2, the conduit 3 and the guide tube 4, as well as the implantable port 9, are identical to those described here above.

In this case, the catheter 5 is formed by a single tube. It includes holes 15 and 16 as previously described above and the related screws engaged in these holes.

The anchoring member 6 is unique and in the form of an extendable tubular portion formed of a zigzag wire made out of a shape memory material, just like for a stent. It is connected to the wire 7 by means of connecting wires 20.

Figure 8:
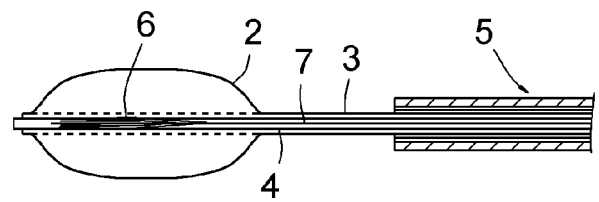
FIG. 8 is a view of this device, with its constituent elements in the assembled-mounted state.
Figure 9:
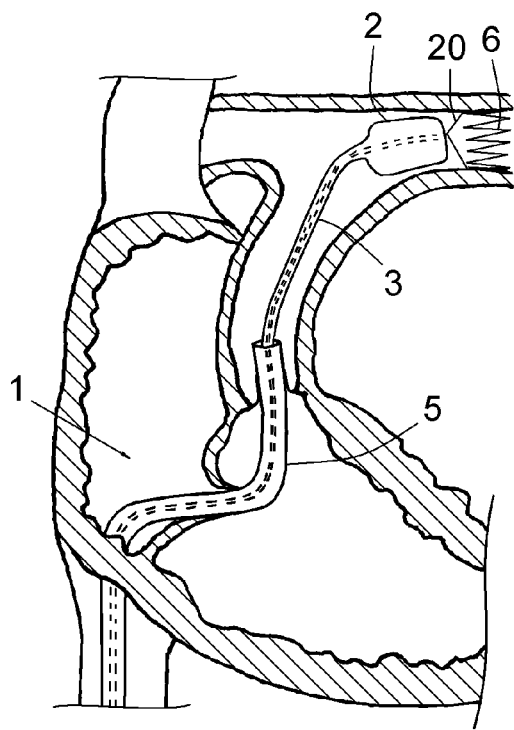
FIG. 9 is a view of a heart similar to that in FIG. 5, during a step in the process to set the device in place.

As shown in FIG. 8, this tubular portion is adapted to be radially contracted down to a contracted position, in which it is capable of being engaged in the guide tube 4 and to slide therein. As shown in FIG. 9, it has, in the deployed position, a diameter greater than the diameter of the left branch of the pulmonary artery.

In practice, the device 1 is introduced into the heart in the same manner as previously described above, then the balloon 2 is deployed from the catheter 5, and the anchoring member 6 is slid into the guide tube 4, up to a position beyond the balloon 2. This anchoring member 6 is then deployed against the wall of the pulmonary artery, so as to immobilise the entire device 1, and therefore the balloon 2, relative to this artery.

Figure 10:
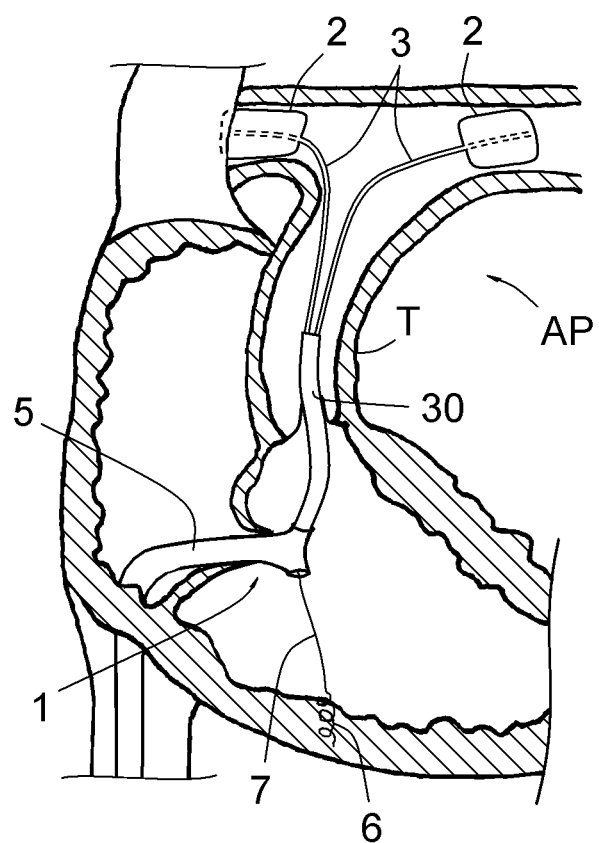
FIG. 10 is a view of a heart similar to that in FIG. 5, during a step in the process to set in place the device according to a third embodiment.

FIG. 10 shows a device 1 according to a third embodiment, comprising two balloons 2, two conduits 3 and two guide tubes 4, a catheter 5, an anchoring member 6 and an actuating wire 7 connected to this anchoring member 6.

In this case, the catheter 5 forms, at its end intended to be inserted into a heart, two openings arranged to open laterally, on two radially opposite sides of the catheter 5. A first opening is intended for letting through a tubular sheath 30 containing the two balloons 2 and the conduits 3 thereof, and the second opening is intended for letting through the anchoring member 6 and the actuating wire 7 connected to this anchoring member.

One of the two balloons 2 is intended to be engaged in the right branch of the pulmonary artery and the other balloon 2 is intended to be engaged in the left branch of the artery, as shown.

The catheter 5 is, in this case, intended to be engaged only in the right ventricle of a heart, with its first opening turned to face the pulmonary valve, in readiness for the deployment of the tubular sheath 30 and the two balloons 2 in the pulmonary artery, through the pulmonary valve, and with its second opening turned towards the wall of the ventricle, and providing the ability to direct the anchoring member 6 to the said wall.

This anchoring member 6 is, in this case constituted by a spring-shaped anchor capable of being inserted in the wall of the ventricle.

The invention thus provides a device for the treatment of pulmonary arterial hypertension further presenting the aforementioned key advantages as compared to similar devices of the prior art.

This invention has been described here above with reference to embodiments provided purely by way of example. It is obvious that it is not limited to these embodiments but extends to all the embodiments described and covered by the appended claims.

The invention claimed is:

1. A system for treating pulmonary hypertension, said system comprising:
   an implantable port configured for subcutaneous implantation and having an internal chamber;
   a guide conduit attached at one end to the implantable port;
   an inflatable balloon attached at another end of the guide conduit to receive an inflation medium therefrom;
   an actuating wire having a distal end with at least one tissue-penetrating element for anchoring within the heart chamber; and
   a catheter having a T-branch that is configured to lie within the heart chamber, wherein (1) one branch of the T extends into the pulmonary artery and has a passage that slidably receives the guide conduit to deploy the guide conduit and the inflatable balloon from the catheter within the pulmonary artery and (2) the other branch of the T has a passage that slidably receives the actuating wire to deploy the at least one tissue-penetrating element from the catheter to anchor the catheter within the heart chamber, wherein the tissue-penetrating element is movable independently of the balloon.

2. A system as in claim 1, further comprising a second guide conduit and a second inflatable balloon which are slidably received in the catheter.

3. A system as in claim 1, further comprising connecting means for connecting the guide conduit and the actuating wire to the catheter, making it possible, in an active position, to block the sliding of the guide conduit and of the actuating wire relative to the catheter, and, in an inactive position, to release this sliding.

4. A system as in claim 3, wherein the connecting means comprise a first set of connecting means making it possible to block the sliding of the conduit in the catheter, and a second set of connecting means, that are capable to be actuated independently from the first set of connecting means, making it possible to block the sliding of the actuating wire.

5. A system as in claim 1, wherein the catheter has two radially opposite sides and said T-branch forms two openings arranged at the ends of the passages to open laterally on said two radially opposite sides of the catheter, wherein a first of the openings is adapted to pass the guide conduit which carries the balloon and a second of the openings is adapted to pass the actuating wire which carries the tissue-penetrating element, the first and second openings being so arranged that, when said first opening is directed towards the pulmonary valve for the deployment of the balloon through the pulmonary valve into the pulmonary artery, the second opening is directed toward the wall of the ventricle in order to direct the tissue-penetrating element toward wall.

6. A system as in claim 5, further comprising a second inflatable balloon.

7. A system as in claim 6, further comprising a second guide conduit which carries the second inflatable balloon.

* * * * *